United States Patent [19]

Sone et al.

[11] Patent Number: 4,787,800

[45] Date of Patent: Nov. 29, 1988

[54] TRANSFER MACHINE IN A SURFACE INSPECTION APPARATUS

[75] Inventors: Kazuyoshi Sone; Katsuya Okumura, both of Kawasaki; Tomio Nakajima; Kanji Ikegaya, both of Tokyo, all of Japan

[73] Assignees: Toshiba Corporation, Kawasaki; Tokyo Kogaku Kikai Kabushiki Kaisha, Tokyo, both of Japan

[21] Appl. No.: 789,088

[22] Filed: Oct. 18, 1985

[30] Foreign Application Priority Data

Oct. 19, 1984 [JP] Japan ................... 59-218297

[51] Int. Cl.⁴ .............................. B65G 1/04
[52] U.S. Cl. ................... 414/222; 269/21; 269/60; 269/73; 414/331; 414/416; 414/752
[58] Field of Search ........... 414/222, 331, 416, 744 B, 414/749, 752; 269/21, 60, 71, 73

[56] References Cited

U.S. PATENT DOCUMENTS

| | | | |
|---|---|---|---|
| 3,272,350 | 9/1966 | Pflaumer et al. | 414/416 |
| 3,823,836 | 7/1974 | Cheney et al. | 414/225 |
| 3,902,615 | 9/1975 | Levy et al. | 414/331 |
| 4,103,232 | 7/1978 | Sugita et al. | 414/36 X |
| 4,318,767 | 3/1982 | Hijikata et al. | 414/225 X |
| 4,402,613 | 9/1983 | Daly et al. | 414/416 X |
| 4,483,651 | 11/1984 | Nakane et al. | 414/222 X |
| 4,550,239 | 10/1985 | Uehara et al. | 414/331 X |
| 4,558,984 | 12/1985 | Garrett | 414/422 X |
| 4,597,708 | 7/1986 | Wheeler et al. | 414/331 |
| 4,695,215 | 9/1987 | Jacoby et al. | 414/752 X |

Primary Examiner—Robert J. Spar
Assistant Examiner—Stuart J. Millman
Attorney, Agent, or Firm—Foley & Lardner, Schwartz, Jeffery, Schwaab, Mack, Blumenthal & Evans

[57] ABSTRACT

A surface inspection apparatus is equipped with a transfer machine which includes a first storage unit for storing a plurality of wafers therein, a first transfer portion for receiving the wafers from the first storage unit one by one and transferring them along a horizontal plane, a first receiver moving vertically between a lower position and an upper position for receiving the wafers from the first transfer portion when the first receiver moves from its lower position to its upper position and moving them up and down, a chuck moving to a predetermined position under the wafers received by the first receiver when the first receiver is at or near its upper position and receiving the inspected elements from the first receiver when the first receiver moves from its upper position to its lower position, the chuck holding the wafers in their fixed condition and moving them in a given direction along a horizontal plane while they are inspected, a second receiver moving vertically between a lower position and an upper position for receiving the wafers from the chuck when the second receiver moves from its lower position to its upper position, a second transfer portion for receiving the wafers from the second receiver when the second receiver moves from its upper position to its lower position and transferring them along a horizontal plane, and a second storage unit for receiving the wafers from the second transfer portion and storing them therein.

34 Claims, 6 Drawing Sheets

FIG. 5
FIG. 6
FIG. 7
FIG. 8
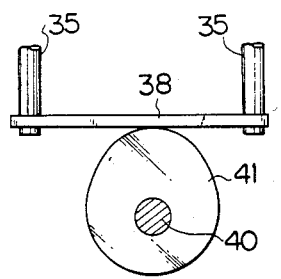
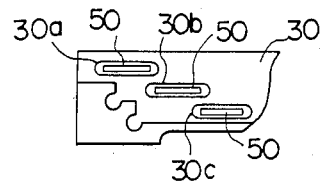
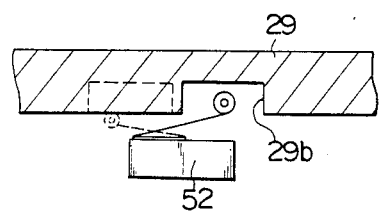
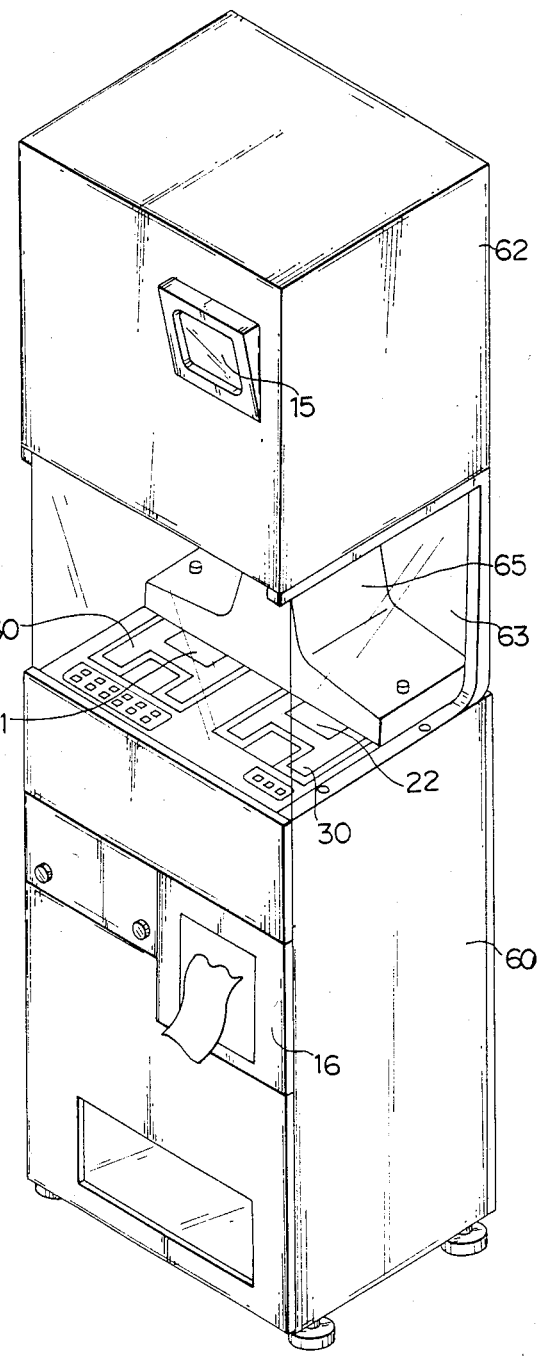

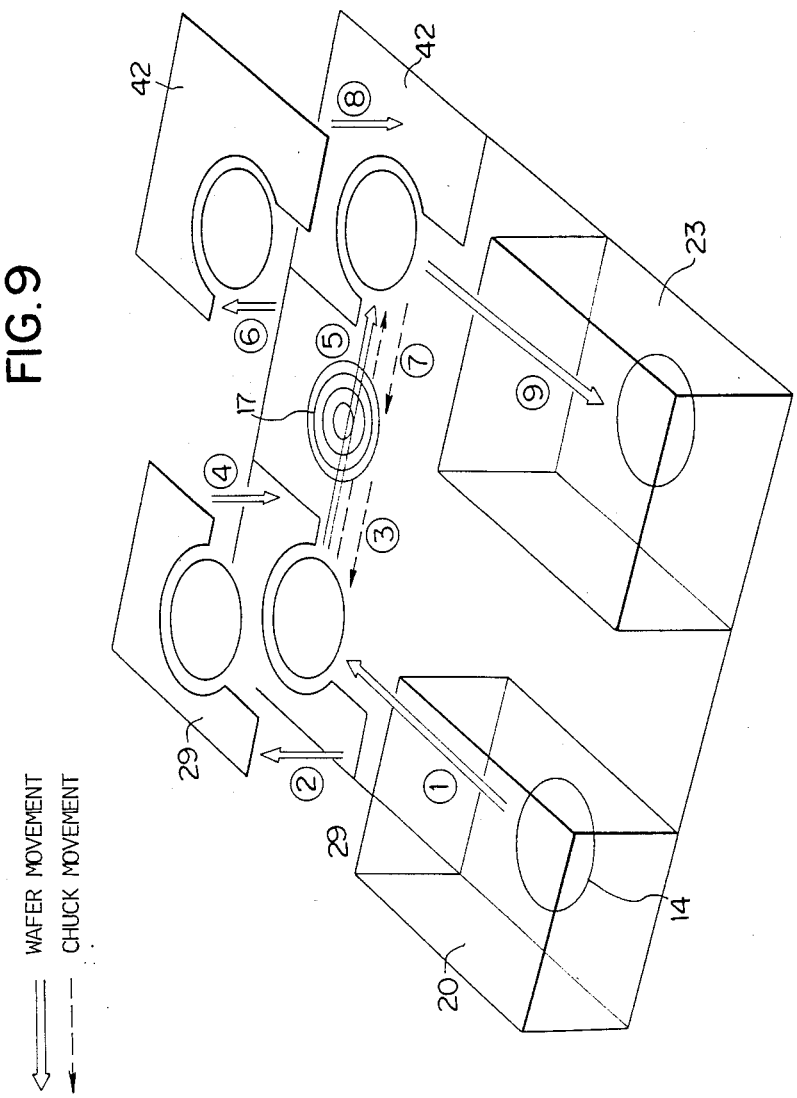

TRANSFER MACHINE IN A SURFACE INSPECTION APPARATUS

BACKGROUND OF THE INVENTION

This invention relates to a transfer machine for transferring inspected elements such as semiconductor wafers from a start point to an end point in a surface inspection apparatus for inspecting undesired particles and abnormalities such as cracks, dirt, foulness or the like on a surface of the semiconductor wafers.

In a conventional surface inspection apparatus, a laser beam is radiated onto a surface of a semiconductor wafer so that the reflected laser beam can be detected thereby to inspect undesired particles and abnormalities such as cracks, dirt, foulness or the like on the surface of the semiconductor wafer. A plurality of wafers are stored in a storage housing such as a carrier or cassette and then taken out thereof one by one in order. Each wafer is transferred to a measuring stage in the surface inspection apparatus while it is tentatively held by a chuck in a fixed condition. At that time, the wafers move at a single grade level along a horizontal plane. After they are inspected at the measuring stage, they are further transferred and then stored in the other storage housing one by one in order.

In general, such a transfer machine must be enlarged in size as wafer sizes become large. Thus, installation space problems occur in practice. In order to solve such problems, various type machines transfer have been proposed.

In the prior art transfer machines, however, the wafers move only at a single grade level along a horizontal plane from one storage housing to the other storage housing. It is very difficult to miniaturize a transfer machine. In fact, effective floor spaces for transfer machines increase because wafer sizes have recently become large.

SUMMARY OF THE INVENTION

The object of this invention is to provide a transfer machine in which a surface inspection apparatus can be miniaturized as a whole by decreasing the size of the transfer machine and in particular its effective floor space.

According to this invention, a surface inspection apparatus is equipped with a transfer machine comprising a first storage housing for storing a plurality of inspected elements therein, a first transfer portion for receiving the inspected elements from the first storage housing one by one in order and transferring them along a horizontal plane, a first receiver moving vertically between a lower positin and an upper position thereof for receiving the inspected elements from the first transfer portion when the first receiver moves from its lower position to its upper position and moving them up and down, a chuck moving to a predetermined position under the inspected elements received by the first receiver when the first receiver is at or near its upper position and receiving the inspected elements from the first receiver when the first receiver comes from its upper position to its lower position, the chuck holding the inspected elements in their fixed condition and moving them in a given direction along a horizontal plane while they are inspected, a second receiver moving vertically between a lower position and an upper position thereof for receiving the inspected elements from the chuck when the second receiver moves from its lower position to its upper position, a second transfer portion for receiving the inspected elements from the second receiver when the second receiver moves from its upper position to its lower position and transferring them along a horizontal plane, and a second storage housing for receiving the inspected elements from the second transfer portion and storing them therein.

It is preferable that the first and second transfer portions are positioned along two opposite sides of an imagined rectangle and the chuck moves along one side of the rectangle, and the first and second receivers and the first and second storage housings are positioned at four corners of the rectangle, respectively.

BRIEF DESCRIPTION OF THE DRAWINGS

This invention will be described in greater detail hereinafter in conjunction with the attached drawings, wherein:

FIG. 5 is a schematic front view, partly in section, showing a part of a mechanism for actuating a receiver for receiving an inspected element such as a semiconductor wafer in the transfer machine;

FIG. 6 is an enlarged plane view showing a portion of the first transfer portion of the transfer machine on which a storage housing is set;

FIG. 7 is a partially sectional view showing means for detecting a receiver for receiving an inspected element;

FIG. 8 is a schematic perspective view showing a surface inspection apparatus equipped with a transfer machine according to this invention; and FIG. 9 is an explanation view showing schematically a course along which semiconductor wafers are transferred by the transfer machine.

DETAILED DESCRIPTION OF THE PREFERRED EMBODIMENT

Figure 1:
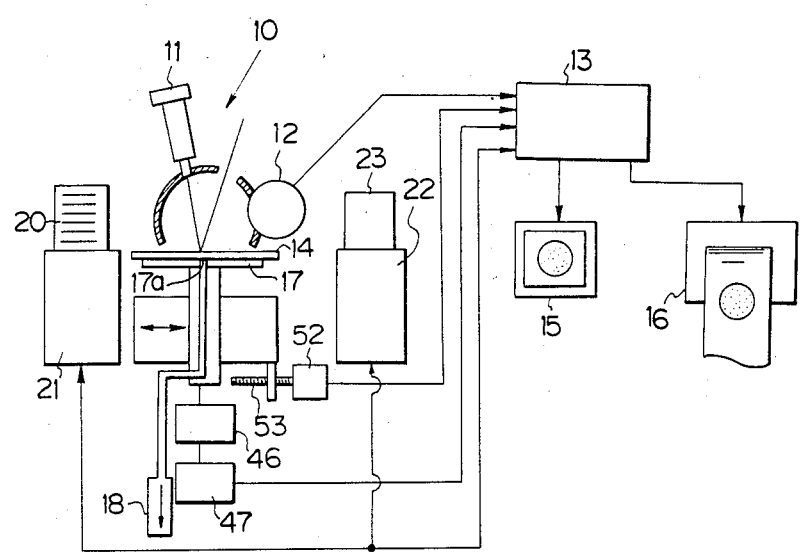
FIG. 1 is a diagrammatic view showing schematically a surface inspection apparatus equipped with a transfer machine according to this invention.

Referring now to FIG. 1, a surface inspection apparatus is equipped with a transfer machine for an inspected element such as a semiconductor wafer or the like.

The surface inspection apparatus has a measuring stage 10 at which a laser beam is radiated from a light source 11 onto an upper surface of a wafer 14 so that the reflected laser beam can be detected. If any abnormality or undesired particle is on the surface of the wafer 14, the scattered light reflected therefrom is detected by a photoelectric transfer element or photoelectric tube 12 such as a photomultiplier tube thereby to produce an electric signal. This electric signal is sent to a control means 13 where any cracks, dirt, foulness or the like on a surface of the wafer 14 are measured as a result of data processing thereof. If desired, these output are displayed at a display unit such as a cathode ray tube 15 and/or printed out by a printer 16 which are connected to the control means 13.

A turntable type chuck 17 holds the wafer 14 in a fixed condition due to its vacuum force. The chuck 17 has a hole 17a connected to a vacuum source 18 in such a way that the wafer 14 can be detachably fixed onto the chuck 17.

A first storage housing 20 is positioned at a start point while a second storage housing 23 is positioned at an end point in the transfer machine. The storage housings may be carriers or cassettes. A plurality of wafers 14 are stored in the first storage housing 20 and taken out thereof one by one in order. Each of the wafers 14 is transferred by a first transfer portion 21 at a single grade level along a horizontal plane from the first storage housing 20 to a first receiver 29. As later described in detail, each wafer 14 is further transferred from the first receiver 29 to the chuck 17 and then fixed thereto. The chuck 17 together with the wafer 14 passes the measuring stage 10 toward a second receiver 42. The wafer 14 is transferred from the chuck to the second receiver 42 and then a second transfer portion 22. The latter transfers the wafer 14 from the second receiver 42 to the second storage housing 23. In such a manner, a plurality of wafers 14 are stored in the second storage housing 23 one by one in order.

Figure 2:
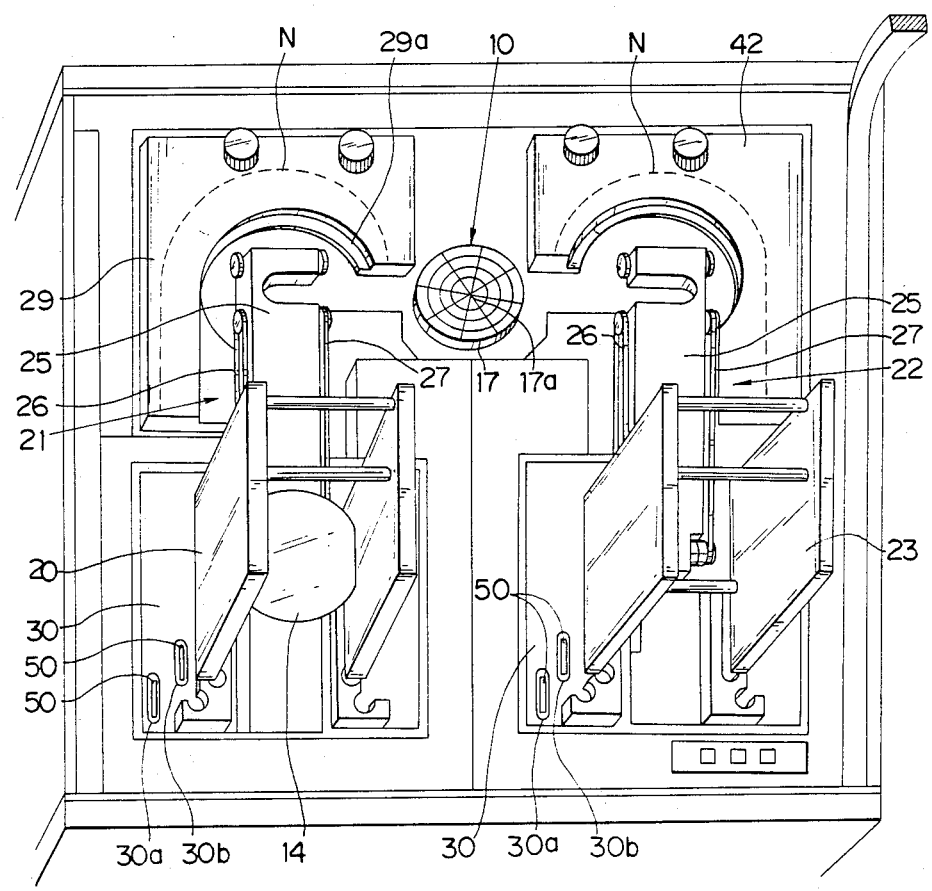
FIG. 2 is a schematic perspective view showing the transfer machine and its related members shown in FIG. 1.
Figure 3:
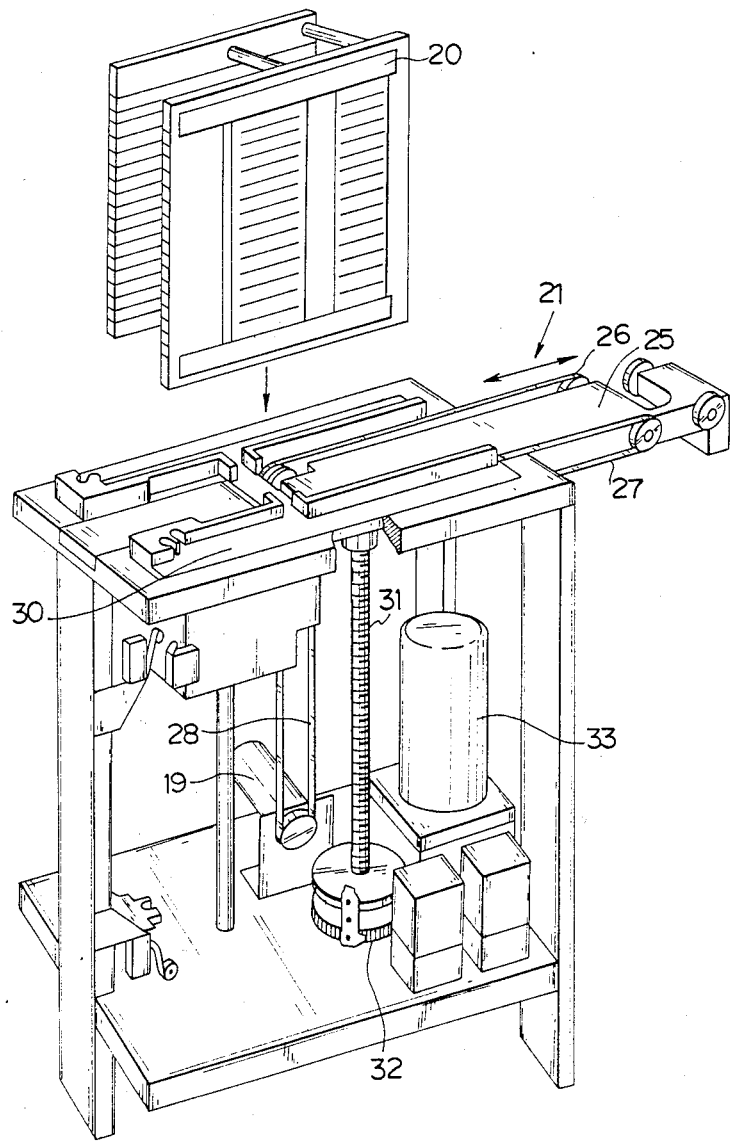
FIG. 3 is a schematic perspective view showing a first storage housing and a first transfer portion of the transfer machine.

As best shown in FIGS. 2 and 3, the first transfer portion 21 has a frame 25 and a pair of endless resilient members 26, 27 placed at either side thereof as a conveyor. The wafer 14 is supported at its edge portion by the transfer members 26, 27 when it is transferred from the first storage housing 20 to the first receiver 29. The transfer members 26, 27 are actuated by a motor 19 through a belt 28.

An elevator 30 is placed at one end of the transfer members 26, 27. The first storage housing 20 is detachably set on a top portion of the elevator 30 in its predetermined position. The top portion of the elevator 30 is formed substantially in a H-shape. The elevator 30 together with the first storage housing 20 moves vertically within a limited range. The elevator 30 is formed with a female screw (not shown) which engages a male screw of a rod 31 vertically extending. The screw rod 31 is connected by way of a gear 32 to a gear (not shown) leading to a motor 33. Thus, the elevator 30 is vertically actuated by the motor 33 through the screw rod 31.

The first receiver 29 is placed at the other end of the transfer members 26, 27 of the first transfer portion 21. The first receiver 29 has a semicircular edge 29a in a step shape corresponding in size to the wafer 14. The peripheral portion of the wafer 14 is partly put in the step-shaped edge 29a whereby the step-shaped edge 29a supports the wafer 14 in a predetermined position after it is transferred to the first receiver 29 by means of the transfer members 26, 27. Also, the step-shaped edge 29a is such formed that it does not interfere with a shaft 45 joined at its top to the chuck 17 as well as the first transfer portion 21.

The first receiver 29 is detachable so that various type receivers can be interchanged in order to adapt them to inspected wafers. For instance, if a relatively large wafer is to be inspected, then a first receiver having a step-shaped edge designated by a dotted line N is used.

The second transfer portion 22 has the same transfer mechanism as the first transfer portion 21. Therefore, the same reference numerals designate the same or corresponding members or parts although they are not described.

Figure 4:
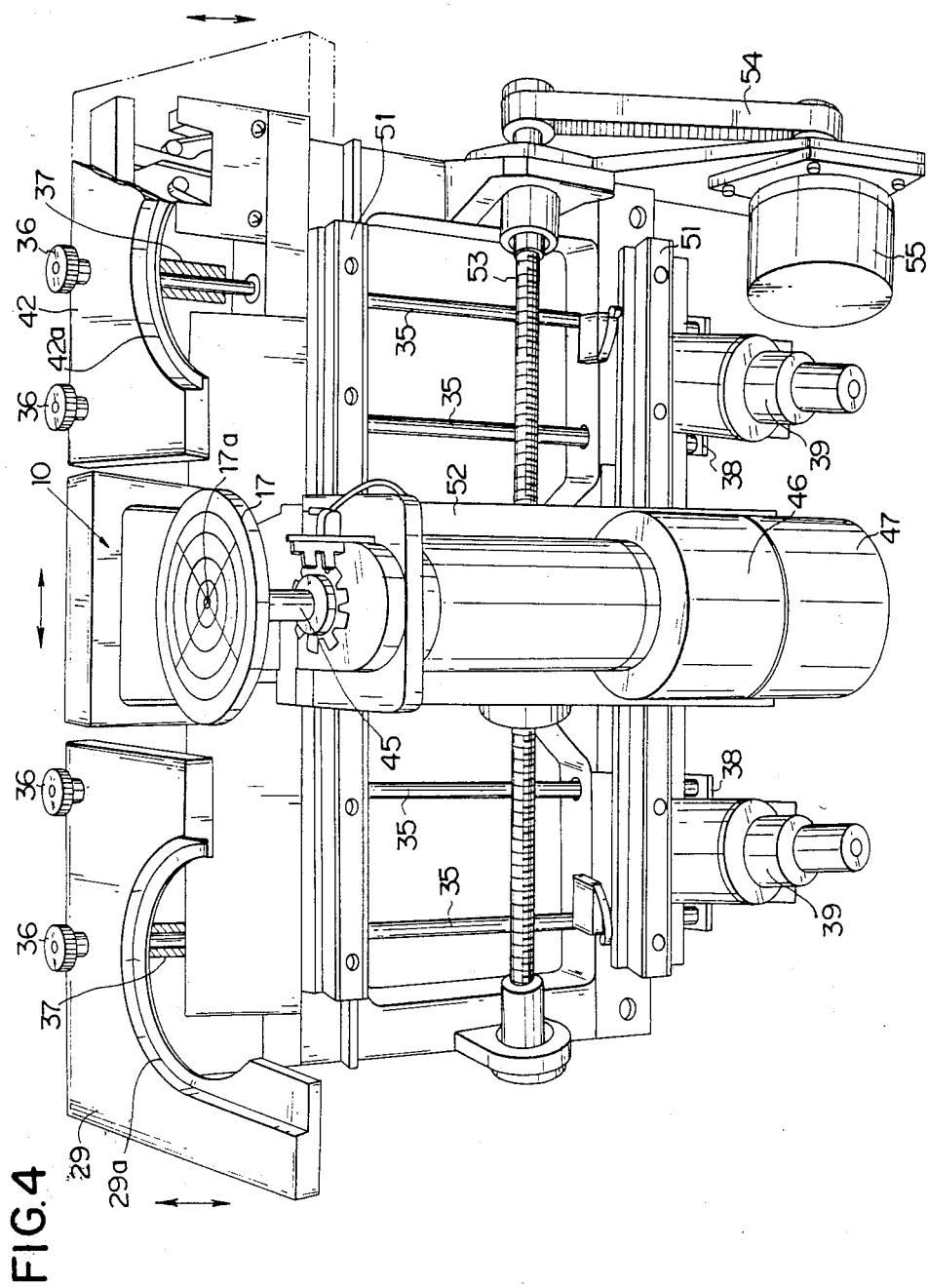
FIG. 4 is a schematic perspective view showing a chuck and its related mechanism in the transfer machine.

As shown in FIGS. 4 and 5, the first receiver 29 is detachably attached to the upper end of two joint rods 35 by means of nuts 36. The joint rods 35 extend vertically in parallel and move up and down along guides 37. The lower end of the joint rods 35 are joined at their lower end to a plate-like follower 38. A shaft 40 of a motor 39 is fixed to an eccentric cam 41 which engages the follower 38. When the eccentric cam 41 is rotated by the motor 39, the joint rods 35 and the first receiver 29 together move up and down.

The second receiver 42 has the same vertical movement mechanism as the first receiver 29. Therefore, the same reference numerals designate the same or corresponding members or parts although they are not described.

In the measuring stage 10, as above-stated, the turntable type chuck 17 has the vacuum hole 17a at its central portion connected to the vacuum source 18. An underside portion of the chuck 17 is fixed to the top of a shaft 45 of a motor 46. An encoder 47 is provided adjacent to the motor 46. The rotation of the motor 46 is transmitted by way of the shaft 45 to the chuck 17 so that the chuck 17 turns at a predetermined speed.

The chuck 17, the motor 46 and others are arranged as a unit so that they can laterally move together along guide rails 51 between the first receiver 29 and the second receiver 42. A male screw rod 53 extends in a lateral direction below the first and second receivers 29, 42 and engages a female screw portion (not shown) fixed to the frame 52. The screw rod 53 is rotatable and connected via a belt 54 to a motor 55 so that the former can be actuated by the latter.

Incidentally, although in the illustrated embodiment the wafer 14 is turned by the chuck 17 when it is transferred at a single grade level along a horizontal plane from the first receiver 29 to the second receiver 42, it is not necessary to turn the wafer 14 if a laser beam to be radiated onto it is scanned.

As shown in FIGS. 2 and 6, means for detecting the shape of the storage housings 20, 23 are provided at the top portion of the elevators 30 of the first and second transfer portions 21, 22, respectively. The detecting means include three elongated openings 30a, 30b, 30c formed in a top portion of each elevator 30 on which a storage housing is set and three microswitches 50 arranged at the corresponding three openings 30a, 30b, 30c so that the shape and in particular the size of the storage housing set thereon can be detected by the microswitches 50. For example, assuming that three different storage housings are to be used, if a large storage housing is set, the microswitch 50 at the outer opening 30a is actuated. If an intermediate storage housing is set, the microswitch 50 at the intermediate opening 30b is actuated. If a small storage housing is set, then the microswitch 50 at the inner opening 30c is actuated. The microswitches 50 are connected electrically to the control means 13 (FIG. 1).

Also, there is provided means for detecting the shape of the first and second receivers 29, 42 and in particular the size of the step-shaped edges 29a, 42a thereof. As shown in FIG. 7, three openings 29b only one of which is shown are formed in each backside portion of the first and second receivers 29, 42. Three microswitches 32 are fixed relative to the guide 37 at or near the three openings 29b and connected to the control means 13. If a certain size of receiver is attached to the joint rods 35, one of the three microswitches 32 is actuated so that the size of the receiver can be detected.

The control means 13 is designed in such a manner that the surface inspection apparatus can operate only when the first and second storage housings 20, 23 match the first and second receivers 29, 42 in shape.

FIG. 8 shows schematically a surface inspection apparatus provided with the above-stated transfer machine. Placed at a lower portion of the surface inspection apparatus is an inspection apparatus body 60 in which the control means 13, the printer 16 and other important members are arranged. The elevators 30, the first transfer portion 21, the second transfer portion 22, the chuck 17 and others are placed at an upper portion of the inspection apparatus body 60. A cover 65 covers the measuring stage 10 at the chuck 17 so that the latter cannot be seen from the outside. A clean unit 62 is fixed above the measuring stage 10. A small clean space 63 is formed between the clean unit 62 and the inspection apparatus body 60. The measuring stage 10 is positioned in the clean space 63 so that the measuring stage 10 is kept very clean in operation. The clean unit 62 is equipped with a well-known air cleaning mechanism so as to blow clean air downwardly. The cover 65 has such a construction that any detrimental light can be prevented from entering the measuring stage 10 and that no turbulent air flow interfering with measurements occurs in the clean space 63 due to such downward clean air blow. Three or four side portions of the clean space 63 are formed of a transparent plate. The front transparent portion thereof can be designed to be opened if desired although not shown in detail.

The cathode ray tube 15 is embedded in the clean unit 62 at a front portion thereof for the purpose of displaying measured results of the wafers 14. The cathode ray tube 15 is slightly inclined downwards so that an operator can easily watch it without any reflected light therefrom.

Referring to FIG. 9, the operation of the transfer machine shown in FIGS. 1 to 7 will be described. First, the first and second storage housings 20, 23 are set on the elevators 30. The first storage housing 20 has plural storage steps on which plural wafers 14 are horizontally stored in a conventional manner. The second storage housing 23 as also plural steps but stores no wafers. An initial condition as shown in FIG. 2 is obtained by pushing a start button at the surface inspection apparatus. In this condition, both storage housings 20, 23 stay at their uppermost position. Next, the first storage housing 20 moves down by one step thereof at the start point whereby the wafer 14 on the lowermost step of the first storage housing 20 is transferred to the first transfer portion 21. On the other hand, the second storage housing 23 moves down to its lowermost position at the end point.

One wafer 14 moves in order from the first storage housing 20 to the transfer members 26, 27 of the first transfer portion 21 whenever the first storage housing 20 moves down by one step thereof. At each time, the wafer 14 is transferred by the transfer members 26, 27 in the direction of an arrow 1. When the wafer 14 moves to the first receiver 29, the first receiver 29 starts to move up in the direction of an arrow 2 whereby the wafer 14 moves from the first transfer portion 21 to the first receiver 29. At that time, the wafer 14 is put in the step-shaped edge 29a. The wafer 14 moves up together with the first receiver 29 in the direction of the arrow 2. Thereafter, the chuck 17 moves under the wafer 14 held by the first receiver 29 in the direction of an arrow 3 and stops there. When the first receiver 29 moves down in the direction of an arrow 4, the wafer 14 moves from the first receiver 29 to the chuck 17. The wafer 14 is tentatively fixed to the chuck 17 due to its vacuum effect. After that, the wafer 14 together with the chuck 17 turns and moves at a given speed in the direction of an arrow 5 while it is inspected at the measuring stage 10 in the above-stated manner. When the wafer 14 moves to the second receiver 42, the vacuum operation stops so that the wafer 14 is released. After that, the second receiver 42 moves up in the direction of an arrow 6 whereby the wafer 14 moves from the chuck 17 to the second receiver 42. At that time, the wafer 14 is put on the step-shaped edge 42a. While the chuck 17 moves back toward the first receiver 29 in the direction of the arrows 3, 7, the second receiver 42 moves down in the direction of an arrow 8. As a result, the wafer 14 moves from the second receiver 42 to the transfer members 26, 27 of the second transfer portion 22. Then the wafer 14 is transferred in the direction of an arrow 9. When the wafer 14 moves to the end point, it enters the second storage housing 23. After that, the second storage housing 23 moves up by one step thereof whereby the wafer 14 moves from the transfer members 26, 27 of the second transfer portion 22 to the uppermost step of the second storage housing 23. Thus, it is stored in the second storage housing 23.

The transfer operation as above-stated is repeated with respect to each of the wafers 14 stored in the first storage housing 20 until all wafers 14 are stored in the second storage housing 23 one by one in order. If the lowermost step of the second storage housing 23 receives the last wafer 14, then the transfer operations end.

Although only one embodiment of this invention has been disclosed and described, it is apparent that other embodiments and modification of this invention are possible. The preferred embodiment described herein is therefore illustrative and not restrictive, the scope of this invention being indicated by the appended claims and all variations which come within the meaning of the claims are intended to be embraced therein.

What is claimed is:

1. A transfer machine for a surface inspection apparatus comprising:
   a first storage means positioned at a first point for storing a plurality of wafers therein;
   a first transfer means for receiving the wafers from the first storage means one by one in order and transferring the wafers;
   a first receiver means for receiving the wafers from the first transfer means one by one, the first receiver means being movable vertically between a lower position and an upper position, so as to receive each of the wafers from the first transfer means at its lower position and moving with the wafer to its upper position;
   a chuck means for receiving each of the wafers from the first receiver means and holding each of the wafers, the chuck means being movable only along a horizontal plane in such a manner that the chuck means can move to a predetermined point positioned under each of the wafers which is received by the first receiver means when the first receiver means is at, or near, its upper position and the chuck means can receive each of the wafers from the first receiver means when the first receiver means moves from its upper position to its lower position;

a second receiver means for receiving each of the wafers from the chuck means, the second receiver means being movable vertically between a lower position and an upper position, for receiving each of the wafers from the chuck means at its lower position and moving with the wafer to its upper position;

a second transfer means for receiving the wafers from the second receiver means one by one and transferring the wafers, the second transfer means being designed to receive each of the wafers from the second receiver means when the second receiver means moves from its upper position to its lower position, so as to transfer the wafers from the second receiver means to the second storage means;

a second storage means for receiving the wafers from the second transfer means one by one in order and storing the wafers therein; and means for moving horizontally the chuck means along a given horizontal moving course between the first receiver means and the second receiver means while the chuck means continues to hold each of the wafers;

wherein the first and second receiver means have a receiving edge for supporting a peripheral portion of each of the wafers, the receiving edge having a cut portion thereof so as to prevent the chuck means from interfering with the first and second receiver means in operation.

2. A transfer machine as defined in claim 1, further comprising a measuring means positioned at an intermediate point of the given horizontal moving course for measuring each of the wafers while the wafers are held by said chuck means.

3. A transfer machine as defined in claim 2, wherein the first and second transfer means are positioned along two opposite sides of an imagined rectangle, and the chuck means holds each of the wafers and moves along one side of the horizontal rectangle which is perpendicular to the two opposite sides while each of the wafers is inspected at the measuring means.

4. A transfer machine as defined in claim 3, wherein the first and second receiver means and the first and second storage means are positioned at four corners of the horizontal rectangle, respectively, and are movable vertically.

5. A transfer machine as defined in claim 1, wherein the chuck means has means for holding the wafers thereto due to a vacuum force.

6. A transfer machine as defined in claim 1, wherein the first storage means stores the wafers in a spaced-apart stacked condition in a vertical direction in such a manner that each of the wafers is put on one of a plurality of steps formed in the first storage means and wherein an elevator moves the first storage means in a vertical direction such that the wafers can move from the first storage means to the first transfer means one by one in order.

7. A transfer machine as defined in claim 1, wherein the second storage means stores the wafers in a spaced-apart stacked condition in a vertical direction in such a manner that each of the wafers is put on one of a plurality of steps formed in the second storage means and wherein an elevator moves the second storage means in a vertical direction such that the wafers can move from the second transfer means to the second storage means one by one in order.

8. A transfer machine as defined in claim 1, wherein the first and second transfer means have endless resilient transfer members, respectively.

9. A transfer machine as defined in claim 1, further comprising turning means for rotating the chuck means.

10. A transfer machine as defined in claim 1 wherein the first transfer means has a first fixed frame and a pair of first endless resilient transfer members placed at either side of the first fixed frame as a conveyor so that the wafers can be supported by the first transfer members when they are transferred from the first storage means to the first receiver means and wherein the second transfer means has a second fixed frame and a pair of second endless resilient transfer members placed at either side of the second fixed frame as a conveyor so that the wafers can be supported by the second transfer members when they are transferred from the second receiver means to the second storage means.

11. A transfer machine as defined in claim 10, further comprising:

a first elevator vertically movable together with the first storage means at one end of the first transfer members in such a way that the wafers can move from the first storage means to the first transfer members one by one; and a second elevator vertically movable together with the second storage means at one end of the second transfer members in such a way that the wafers can move from the second transfer members to the second storage means one by one.

12. A transfer machine for a surface inspection apparatus comprising:

a first storage means positioned at a first point for storing a plurality of wafers therein;

a first transfer means for receiving the wafers from the first storage means one by one in order and transferring the wafers;

a first receiver means for receiving the wafers from the first transfer means one by one, the first receiver means being movable vertically between a lower position and an upper position, so as to receive each of the wafers from the first transfer means at its lower position and moving with the wafer to its upper position;

a chuck means for receiving each of the wafers from the first receiver means and holding each of the wafers, the chuck means being movable only along a horizontal plane in such a manner that the chuck means can move to a predetermined point positioned under each of the wafers which is received by the first receiver means when the first receiver means is at, or near, its upper position and the chuck means can receive each of the wafers from the first receiver means when the first receiver means moves from its upper position to its lower position;

a second receiver means for receiving each of the wafers from the chuck means, the second receiver means being movable vertically between a lower position and an upper position, for receiving each of the wafers from the chuck means at its lower position and moving with the wafer to its upper position;

a second transfer means for receiving the wafers from the second receiver means one by one and transferring the wafers, the second transfer means being designed to receive each of the wafers from the second receiver means when the second receiver means moves from its upper position to its lower position, so as to transfer the wafers from the second receiver means to the second storage means;

a second storage means for receiving the wafers from the second transfer means one by one in order and storing the wafers therein; and means for moving horizontally the chuck means along a given horizontal moving course between the first receiver means and the second receiver means while the chuck means continues to hold each of the wafers;

wherein the first transfer means has a first fixed frame and a pair of first endless resilient transfer members placed at either side of the first fixed frame as a conveyor so that the wafers can be supported by the first transfer members when they are transferred from the first storage means to the first receiver means and wherein the second transfer means has a second fixed frame and a pair of second endless resilient transfer members placed at either side of the second fixed frame as a conveyor so that the wafers can be supported by the second transfer members when they are transferred from the second receiver means to the second storage means; and wherein the first receiver means is vertically movable at an end of the first transfer members and has a semicircular edge in a step shape corresponding in size to each of the wafers so that the semicircular edge can support a peripheral portion of each of the wafers and wherein the second receiver means is vertically movable at an end of the first transfer members and has a semicircular edge in a step-shape corresponding in size to each of the wafers so that the semicircular edge can support a peripheral portion of each of the wafers.

13. A transfer machine as defined in claim 12, wherein the first and second receiver means are detachable so that receiver means of various design can be interchanged.

14. A transfer machine as defined in claim 9, wherein the turning means includes a movable frame, a motor attached to the movable frame and a shaft rotated by the motor and wherein the chuck means is fixed to a top portion of the shaft.

15. A transfer machine for a surface inspection apparatus comprising:

a first storage means positioned at a first point for storing a plurality of wafers therein;

a first transfer means for receiving the wafers from the first storage means one by one in order and transferring the wafers;

a first receiver means for receiving the wafers from the first transfer means one by one, the first receiver means being movable vertically between a lower position and an upper position, so as to receive each of the wafers from the first transfer means at its lower position and moving with the wafer to its upper position;

a chuck means for receiving each of the wafers from the first receiver means and holding each of the wafers, the chuck means being movable only along a horizontal plane in such a manner that the chuck means can move to a predetermined point positioned under each of the wafers which is received by the first receiver means when the first receiver means is at, or near, its upper position and the chuck means can receive each of the wafers from the first receiver means when the first receiver means moves from its upper position to its lower position;

a second receiver means for receiving each of the wafers from the chuck means, the second receiver means being movable vertically between a lower position and an upper position, for receiving each of the wafers from the chuck means at its lower position and moving with the wafer to its upper position;

a second transfer means for receiving the wafers from the second receiver means one by one and transferring the wafers, the second transfer means being designed to receive each of the wafers from the second receiver means when the second receiver means moves from its upper position to its lower position, so as to transfer the wafers from the second receiver means to the second storage means;

a second storage means for receiving the wafers from the second transfer means one by one in order and storing the wafers therein;

means for moving horizontally the chuck means along a given horizontal moving course between the first receiver means and the second receiver means while the chuck means continues to hold each of the wafers; and turning means for rotating the chuck means;

wherein the turning means includes a movable frame, a motor attached to the movable frame and a shaft rotated by the motor and wherein the chuck means is fixed to a top portion of the shaft; and wherein the movable frame, the shaft, the motor and the chuck means are assembled as a unit which is movable between the first receiver means and the second receiver means.

16. A transfer machine as defined in claim 9, wherein the moving means includes a screw rod extending in a lateral direction between the first receiver means and the second receiver means in such a manner that the turning means can be actuated by the screw rod so as to move both the chuck means and the turning means between the first receiver means and the second receiver means.

17. A transfer machine as defined in claim 15, wherein the movable frame has female screw portion and wherein the moving means includes a male screw rod extending in a lateral direction between the first receiver means and the second receiver means for engaging the female screw portion of the movable frame in such a manner that the turning means can be actuated by the screw rod so as to move both the chuck means and turning means between the first receiver means and the second receiver means.

18. A transfer machine for a surface inspection apparatus comprising:

a first transfer means for transferring a plurality of wafers;

a first receiver means for receiving each of the wafers from the first transfer means;

a chuck means having a central portion for holding each of the wafers and transferring the wafers;

a second receiver means for receiving each of the wafers from the chuck means;

a second transfer means for receiving each of the wafers from the second receiver means and transferring the wafers;

turning means joined to the chuck means for turning the chuck means about a vertical axis which is located at the center of the central portion of the chuck means;

means for moving both of the chuck means and the turning means along a given horizontal course between the first receiver means and the second receiver means while the chuck means continues to hold each of the wafers; and means for guiding the turning means in such a manner that the turning means can move along the horizontal course;

wherein the turning means includes a movable frame, a motor attached to the movable frame and a shaft joined to the motor and wherein the chuck means is fixed to a top portion of the shaft; and wherein the movable frame, the shaft, the motor and the chuck means are assembled as a unit and move together between the first receiver means and the second receiver means.

19. A transfer machine as defined in claim 18, wherein the moving means includes a screw rod extending in a lateral direction between the first receiver means and the second receiver means in such a manner that the turning means can be actuated by the screw rod so as to move between the first receiver means and the second receiver means.

20. A transfer machine as defined in claim 18, wherein the movable frame has a female screw portion and wherein the moving means includes a male screw rod extending in a lateral direction between the first receiver means and the second receiver means for engaging the female screw portion of the movable frame in such a manner that the turning means can be actuated by the screw rod so as to move between the first receiver means and the second receiver means.

21. A transfer machine as defined in claim 18, wherein the means for guiding includes a pair of guide rails extending laterally between the first receiver means and the second receiver means.

22. A transfer machine as defined in claim 18, further comprising means for measuring each of the wafers by radiating a laser beam onto each of the wafers while the chuck means holds each of the wafers, the measuring means being positioned at an intermediate point of the horizontal moving course.

23. A transfer machine as defined in claim 22, wherein the measuring means is placed in a clean space so that the measuring means can be kept clean in operation.

24. A transfer machine as defined in claim 23, wherein the clean space is formed between a clean unit and an inspection apparatus body.

25. A transfer machine as defined in claim 24, wherein the measuring means is covered by a cover.

26. A transfer machine as defined in claim 24, further comprising:

a first storage means for storing the wafers, the first transfer means being adapted to receive the wafers from the first storage means; and a second storage means for receiving the wafers from the second transfer means;

wherein the first transfer means, the second transfer means and the chuck means are placed at an upper portion of the inspection apparatus body.

27. An apparatus for inspecting a plurality of test articles, comprising a transfer machine for transferring the test articles, a source for radiating a laser beam to each of the test articles while the test article is transferred by the transfer machine, so that the laser beam can be reflected by each test article, means for detecting the laser beam reflected thereby and producing an electrical signal and a control means for receiving the electrical signal from the detecting means, wherein the transfer machine comprises:

a chuck means having a central portion for holding each of the test articles;

moving means for moving the chuck means and the test article along a given horizontal course so that the chuck means can move only in a horizontal direction while the chuck means continues to hold the test article;

means for turning the chuck means together with the test article about a vertical axis which is located at the center of the central portion of the chuck means; and means for guiding the turning means;

wherein the guiding means includes a pair of guide rails extending laterally between a first receiver means and a second receiver means and said chuck means transfer the test articles between said first receiver means and said second receiver means.

28. The transfer machine of claim 27, wherein the radiating source source is positioned at an intermediate portion of the moving course.

29. The transfer machine of claim 27, wherein the radiating source source is fixed.

30. The transfer machine of claim 27, wherein the chuck means includes a vacuum means for holding the test article due to its vacuum force.

31. A transfer machine as defined in claim 27, wherein the turning means includes a movable frame, a motor attached to the movable frame and a shaft joined to the motor and wherein the chuck means is fixed to a top portion of the shaft.

32. A transfer machine as defined in claim 37, wherein the movable frame, the shaft, the motor and the chuck means are assembled as a unit which is movable between a first receiver means and a second receiver means.

33. A transfer machine as defined in claim 27, wherein the moving means includes a screw rod extending in a lateral direction between a first receiver means and a second receiver means in such a manner that the turning means can be actuated by the screw rod so as to move both the chuck means and turning means between the first receiver means and the second receiver means.

34. A transfer machine as defined in claim 31, wherein the movable frame has a female screw portion and wherein the moving means includes a male screw rod extending in a lateral direction between the first receiver means and the second receiver means for engaging the female screw portion of the movable frame in such a manner that the turning means can be actuated by the screw rod so as to move between the first receiver means and the second receiver means.

* * * * *